United States Patent [19]

Storer

[11] 4,315,006
[45] Feb. 9, 1982

[54] BENZOXOCIN DERIVATIVES HAVING ANXIOLYTIC AND ANTI-CONVULSANT ACTIVITIES

[75] Inventor: Richard Storer, Wembley, England

[73] Assignee: Glaxo Group Limited, London, England

[21] Appl. No.: 176,537

[22] Filed: Aug. 8, 1980

[30] Foreign Application Priority Data

Aug. 9, 1979 [GB] United Kingdom ............... 27800/79
May 1, 1980 [GB] United Kingdom ............... 14559/80

[51] Int. Cl.³ .................. C07D 311/78; A61K 31/35; C07D 405/04
[52] U.S. Cl. ............................... 424/250; 260/345.2; 544/378; 546/196; 424/267; 424/283
[58] Field of Search ...................... 260/345.2; 546/196; 544/375, 378; 424/283, 250, 267

[56] References Cited

U.S. PATENT DOCUMENTS 3,869,475 3/1975 Mechoulam et al. ............. 260/345.2
4,140,701 2/1979 Ryan ................................. 260/345.2

Primary Examiner—Nicky Chan
Attorney, Agent, or Firm—Bacon & Thomas

[57] ABSTRACT

Compounds are disclosed of general formula

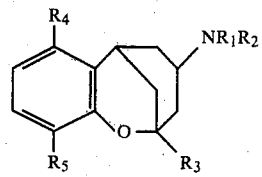

wherein $R_1$ represents a hydrogen atom or $C_{1-4}$ alkyl or $C_{2-4}$ alkenyl group, or the group $COANH_2$, $CSANH_2$, or $COANHCOCH_2NH_2$ in which A is methylene optionally substituted by a $C_{1-3}$ alkyl group; and $R_2$ represents a hydrogen atom or a $C_{1-4}$ alkyl group; or $NR_1R_2$ forms a piperidino, piperazino or N-methylpiperazino group;

$R_3$ represents a $C_{1-4}$ alkyl group or a benzyl group;

$R_4$ represents a hydrogen or halogen atom; and $R_5$ represents a hydrogen atom or a $C_{1-4}$ alkyl or $C_{1-4}$ alkoxy group, with the proviso that one of $R_4$ and $R_5$ is a hydrogen atom and physiologically acceptable salts and bioprecursors thereof.

The compounds exert effects on the central nervous system and, in particular exhibit anxiolytic and anti-convulsant activity. The compounds may be formulated with pharmaceutically acceptable carriers or diluents for administration in conventional manner.

9 Claims, No Drawings

BENZOXOCIN DERIVATIVES HAVING ANXIOLYTIC AND ANTI-CONVULSANT ACTIVITIES

This invention relates to benzoxocin derivatives, to processes for their preparation, to pharmaceutical preparations containing them and to their use in medicine.

It has been found that certain benzoxocin derivatives have a valuable pharmacolgial activity, in particular on the central nervous system, as more particularly described hereinafter.

The present invention provides compounds of the general formula I

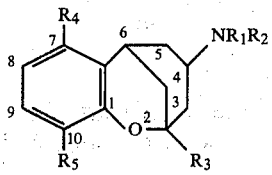

wherein $R_1$ represents a hydrogen atom or a $C_{1-4}$ alkyl or $C_{2-4}$ alkenyl group, or the group $COANH_2$, $CSANH_2$, or $COANHCOCH_2NH_2$ in which A is methylene optionally substituted by a $C_{1-3}$ alkyl group; and $R_2$ represents a hydrogen atom or a $C_{1-4}$ alkyl group; or $NR_1R_2$ forms a piperidino, piperazino or N-methylpiperazino group;

$R_3$ represents a $C_{1-4}$ alkyl or benzyl group;

$R_4$ represents a hydrogen or halogen atom; and $R_5$ represents a hydrogen atom or a $C_{1-4}$ alkyl or $C_{1-4}$ alkoxy group with the proviso that one of $R_4$ and $R_5$ is hydrogen and physiologically acceptable salts and bioprecursors thereof.

The compounds according to the invention readily form physiologically acceptable salts, in particular acid addition salts. Such salts include salts with inorganic acids such as hydrochlorides, hydrobromides and sulphates, and salts with organic acids such as acetates, tartrates, citrates, maleates and fumarates.

As used herein the term "physiologically acceptable bioprecursor" of a drug means a compound having a structural formula different from the drug but which, upon administration to an animal or human being, is converted in the patient's body to the drug.

The compounds of the invention have the β-configuration at the 4-position and also have centres of asymmetry at the 2- and 6-positions. Thus a compound of the invention may exist as a racemic modification or as one of its two enantiomers. The racemic modification may be resolved into its two enantiomers by conventional procedures for example by using a suitable optically active acid such as (+) tartaric acid.

Preferred meanings for the groups $R_1$-$R_5$ are as follows:

| | |
|---|---|
| $R_1$ | hydrogen, alkyl e.g. methyl or ethyl, aminoacetyl, 2-aminopropionyl or glycyglycyl, and more particularly hydrogen or aminoacetyl; |
| $R_2$ | hydrogen or alkyl e.g. methyl or ethyl, more particularly hydrogen; |
| $NR_1R_2$ | piperidino; |
| $R_3$ | alkyl e.g. methyl or ethyl, more particularly methyl; |
| $R_4$ | hydrogen or chlorine, more particularly hydrogen; |
| $R_5$ | hydrogen or alkoxy e.g. methoxy or ethoxy, more particularly hydrogen. |

Preferred compounds according to the invention are 4β-amino-3,4,5,6-tetrahydro-2,6-methano-2-methyl-1-benzoxocin and 4β-aminoacetylamino-3,4,5,6-tetrahydro-2,6-methano-2-methyl-1-benzoxocin and their physiologically acceptable salts, of which the latter, especially as its levorotatory(−)enantiomer, is particularly preferred.

The compounds according to the invention exert effects on the central nervous system (CNS) and, in particular, exhibit anxiolytic and anticonvulsant acitivity.

The CNS activity of the compounds has been demonstrated by their action, in mice, in the antinicotine test on the basis of the method described by Aceto, Bentley and Dembinski (Br. J. Pharmac. 1969, 37, 104–111). Convulsions are induced by the intravenous injection of nicotine, the end point of the test being taken as the toxic extensor convulsion.

The anxiolytic and anti-convulsant properties of the benzoxocin derivatives have been demonstrated by their activity, in mice, in the anti-rage and maximal electroshock tests according to the procedures described by Tedeschi et al (J. Pharmac. Exp. Ther. 125, 28–34) and Swinyard et al (J. Pharmac. Exp. Ther. 106, 319–330) respectively.

The compounds according to the invention can be administered orally or parenterally or by suppository, of which the preferred route is the oral route. They may be used in the form of the base or as a physiologically acceptable salt. They will in general be associated with a pharmaceutically acceptable carrier or diluent, to provide a pharmaceutical composition.

For oral administration the pharmaceutical composition can most conveniently be in the form of capsules or tablets, including slow release preparations. The composition may also take the form of a dragee or may be in the form of a syrup or a suspension in an aqueous or non-aqueous vehicle.

A convenient daily dose by the oral route would be of the order of 10–500 mg per day, in the form of dosage units containing from 10 to 200 mg of active ingredient per dosage unit. A convenient regimen in the case of a slow release capsule or tablet would be once or twice a day.

Parenteral administration may be by injections at intervals or as a continuous infusion. Injection solutions may contain from 1 to 100 mg/ml of active ingredient.

Suppositories may be formulated using conventional suppository bases such as cocoa butter or other glyceride.

A compound of general formula (I) in which $R_1$ and $R_2$ represent hydrogen atoms may be prepared by reducing an oxime of general formula (II):

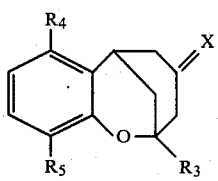

in which X is the group $NOR_6$ where $R_6$ is a hydrogen atom or an acyl or alkyl group.

Reduction may be effected using a metallic reagent, in particular an alkali metal (e.g. sodium or lithium), in a suitable medium, particularly an alcohol and/or liquid ammonia. Preferred reaction conditions involve reacting the oxime with sodium or lithium metal in solution in 1-propanol, tetrahydrofuran and anhydrous ammonia. Other reaction conditions include the use of sodium metal in an alkanol such as 1-propanol.

Reduction may also be effected using other reducing agents such as complex metal hydrides, for example lithium aluminium hydride.

The oxime of general formula (II) above may be prepared from the corresponding 4-ketone of formula (II) but in which X is oxygen. Thus, reaction with hydroxylamine gives the oxime (II) in which $R_6$ is hydrogen, and this may then be acylated, for example with an appropriate acid anhydride in pyridine, to give a derivative of general formula (II) in which $R_6$ is an acyl group, particularly acetyl. Alternatively an oxime derivative of formula (II) in which $R_6$ is an alkyl group, particularly methyl, may be prepared by reaction of the 4-ketone (X=O in general formula (II)) with an O-substituted hydroxylamine, such as O-methyl hydroxylamine, to give the corresponding O-alkyl oxime.

The preparation of compounds in which the group $-NR_1R_2$ is not formed directly in the above described reaction may in general be effected by further modification of the compound in which $-NR_1R_2$ represents $-NH_2$, using conventional procedures. Thus, acylation with, for example, an acid chloride or anhydride affords a mono-acylamino compound which may be reduced with, for example, diborane or lithium aluminium hydride to give the corresponding mono-alkylated amino product. This in turn may be further alkylated to give a dialkylamino compound (in which $R_1$ and $R_2$ may be the same or different). Monoalkylation and dialkylation (e.g. dimethylation using formaldehyde and formic acid) may also be effected directly on the parent amine.

Derivatives in which $R_1$ is an alkenyl group are prepared by reaction of the parent amine compound with a conventional reagent such as an alkenyl halide, for example, allyl bromide. Compounds in which the group $-NR_1R_2$ forms a piperidino, piperazino or N-methylpiperazino group may be prepared by reaction of the 4-aminobenzoxocin with a dihalo-compound such as $Br(CH_2)_5Br$.

For the preparation of compounds of the invention in which $R_1$ is a group $-COANH_2$, the parent 4-aminobenzoxocin may be treated with a haloacyl (e.g. bromoacyl)halide to given an intermediate containing the group $-NHCOA(Hal)$. The halogen atom (Hal) is then replaced by the group $-NH_2$ by reaction with ammonia. A suitable solvent for this reaction is an alcohol such as methanol.

Alternatively compounds of formula I in which $R_1$ is a group $-COANH_2$ or $-COANHCOCH_2NH_2$ may in general be prepared by conventional methods used in peptide synthesis. Thus for example a 4-aminobenzoxo-cin may be acylated with a protected amino acid, with subsequent removal of the protecting group.

Compounds of the invention in which $R_1$ is a group $-CSANH_2$, may be prepared by treatment of the corresponding compound in which $R_1$ is a group $-COANH_2$ with, for example, phosphorous pentasulphide.

The 4-ketones of general formula (II) in which X is oxygen may be prepared from salicylaldehyde or an appropriately substituted salicylaldehyde of general formula (III):

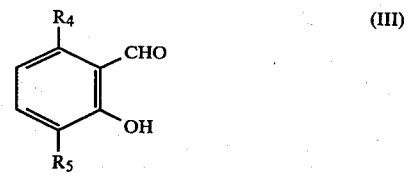

by reaction with a ketone $(CH_3COR_3)$, in particular acetone, in the presence of a base to give a butenone of formula (IV):

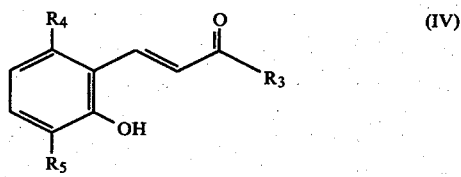

which may be converted into the desired 4-ketone (II) by further reaction with ethyl acetoacetate or acetylacetone, again under basic conditions.

Where the product of any of the processes just described is a free base and a salt is required, the salt may be formed in conventional manner. For example, a generally convenient method of forming the salts is to mix appropriate quantities of the free base and the acid in an appropriate solvent or mixture of solvents, e.g. an ether such as diethyl ether, an alcohol such as ethanol or an ester such as ethyl acetate.

In order that the invention may be more fully understood, the following Examples are given by way of illustration only.

EXAMPLE 1

4β-Amino-3,4,5,6-tetrahydro-2,6-methano-2-methyl-1-benzoxocin hydrochloride

Method A

A solution of 3,4,5,6-tetrahydro-2,6-methano-2-methyl-4-oxo-1-benzoxocin oxime (2.0 g) in 1-propanol (140 ml) was stirred and heated under reflux. Sodium metal (6.42 g) was added over a 1 h period and when reaction was complete the mixture was evaporated almost to dryness. The residue was treated with water (100 ml) and the aqueous mixture was extracted with ether. The extracts were shaken with 2N-hydrochloric acid, the acid solution was separated, made basic by the addition of sodium hydroxide solution and extracted with ether. The ethereal extracts were dried ($MgSO_4$) and the solvent was evaporated under reduced pressure.

The residual oil, in dry ether, was treated with excess hydrogen chloride from a standard ethanolic solution. The solid product was collected by filtration and recrystallised from a mixture of ethanol and ethyl acetate to afford the title compound (0.52 g) as small colourless needles, m.p. 330° (Found: C, 64.9; H, 7.8; N, 5.6; Cl, 14.6. $C_{13}H_{18}ClNO$ requires C, 65.1; H, 7.6; N, 5.8; Cl, 14.8%.)

Method B 3,4,5,6-Tetrahydro-2,6-methano-2-methyl-4-oxo-1-benzoxocin oxime (20 g) was dissolved in tetrahydrofuran (200 ml) and the solution added to liquid ammonia (400 ml) contained in a flask fitted with a Drikold-cooled condenser. n-Propanol (18 ml) was added and the mixture was stirred for 10 minutes. Lithium (2.9 g) was then added slowly over a period of 3.5 hours. The ammonia was allowed to evaporate and most of the THF was removed under reduced pressure. The residue was diluted with water (200 ml) and extracted with diethyl ether (2×150 ml). The combined extracts were dried ($MgSO_4$) and treated with conc. hydrochloric acid (8 ml) over 10 minutes. The dense white solid was filtered off, washed with ether and dried under reduced pressure at 40° for several hours to give the title compound (16.9 g) m.p. 320°–322°. (Found: C, 63.6; H, 7.6; Cl, 14.3; N, 5.6% Calc. for $C_{13}H_{18}NOCl.\frac{1}{2}H_2O$: C, 63.0; H, 7.6; Cl, 14.3; N, 5.6%.)

EXAMPLE 2

4β-Dimethylamino-3,4,5,6-tetrahydro-2,6-methano-2-methyl-1-benzoxocin hydrochloride A solution of 4β-amino-3,4,5,6-tetrahydro-2,6-methano-2-methyl-1-benzoxocin (0.24 g) in a mixture of 98% formic acid (1.05 ml) and 37% aqueous formaldehyde (1.8 ml) was refluxed for 30 min and allowed to cool. The mixture was diluted with water (3 ml), made basic by the addition of sodium hydroxide solution and extracted with ether. The extracts were dried ($MgSO_4$) and the solvent was evaporated.

The residue, in dry ether, was treated with excess ethanolic hydrogen chloride. The resulting solid was collected by filtration and recrystallised from 2-propanol to afford the title compound (0.17 g) as white needles, m.p. 260°–262°. (Found: C, 67.1; H, 8.1; N, 4.9; Cl, 12.9. $C_{15}H_{22}ClNO$ requires C, 67.3; H, 8.3; N, 5.2; Cl, 13.2%.)

EXAMPLE 3

4β-Formylamino-3,4,5,6-tetrahydro-2,6-methano-2-methyl-1-benzoxocin

A solution of 4β-amino-3,4,5,6-tetrahydro-2,6-methano-2-methyl-1-benzoxocin (2.6 g) in 98% formic acid (30 ml) was stirred and heated to 55°. Acetic anhydride (10 ml) was added dropwise and the mixture was stirred at 55° for 1 h and diluted to 600 ml by the addition of water. The aqueous mixture was saturated with sodium chloride and extracted with ether. The extracts were washed with saturated sodium bicarbonate solution and water, dried ($MgSO_4$) and the solvent was evaporated. The solid residue was recrystallised from ethyl acetate to afford the title compound (2.05 g) as colourless prisms m.p. 154°–156°.

EXAMPLE 4

3,4,5,6-tetrahydro-2,6-methano-2-methyl-4β-methylamino-1-benzoxocin hydrochloride A suspension of 4β-formylamino-3,4,5,6-tetrahydro-2,6-methano-2-methyl-1-benzoxocin (1.77 g) in dry ether (100 ml) was added to a suspension of lithium aluminium hydride (0.6 g) in dry ether (50 ml). The mixture was stirred and refluxed for 2 h, cooled in an ice-bath and treated with water. The mixture was filtered and the filtrate was separated into organic and aqueous phases. The aqueous phase was saturated with sodium chloride and extracted with ether. The ethereal solutions were combined and washed with 2N-hydrochloric acid. The acid washings were made basic by the addition of sodium hydroxide solution and extracted with ether. The extracts were dried ($MgSO_4$) and the solvent was evaporated to afford an oil (1.54 g).

The oil, in dry ether, was treated with excess ethanolic hydrogen chloride. The solid was collected by filtration and recrystallised from 1-propanol to afford the title compound (1.4 g) as white plates m.p. 278°–280°. (Found: C, 66.6; H, 8.0; N, 5.7; Cl, 13.95. $C_{14}H_{20}ClNO$ requires C, 66.3; H, 7.9; N, 5.5; Cl, 14.0%.)

EXAMPLE 5

3,4,5,6-Tetrahydro-2,6-methano-2-methyl-4β-piperidino-1-benzoxocin hydrochloride A solution of 4β-amino-3,4,5,6-tetrahydro-2,6-methano-2-methyl-1-benzoxocin (1.8 g) and 1,5-dibromopentane (3.06 g) in ethanol (60 ml) was treated with anhydrous potassium carbonate (5.58 g) and the mixture was stirred and refluxed for 7 h. A further addition of 1,5-dibromopentane (1.0 g) was made and the reaction was continued for a further 4 h. The reaction mixture was allowed to cool to room temperature, water (60 ml) was added and the mixture was extracted with ether. The extracts were washed with 2N-hydrochloric acid and the acid washings were made basic by the addition of sodium hydroxide solution and extracted with ether. The extracts were dried ($MgSO_4$) and the solvent was evaporated to afford a yellow solid (1.77 g).

The product, in dry ether, was treated with excess ethanolic hydrogen chloride. The resulting solid was collected by filtration and recrystallised from dioxan to afford the title compound (0.74 g) as colourless needles m.p. 251°–255°. (Found: C, 70.0; H, 8.75; N, 4.6; Cl, 11.5. $C_{18}H_{26}ClNO$ requires C, 70.2; H, 8.5; N, 4.55; Cl, 11.5%.)

EXAMPLE 6

4β-Acetylamino-3,4,5,6-tetrahydro-2,6-methano-2-methyl-1-benzoxocin

4β-Amino-3,4,5,6-tetrahydro-2,6-methano-2-methyl-1-benzoxocin (2.5 g) and triethylamine (2.5 g) were dissolved in dry ether. The stirred solution was cooled in an ice-bath, treated dropwise with acetyl chloride (2.65 g) in dry ether (25 ml) and the mixture was stirred 2 h at room temperature. Water (200 ml) was added and the mixture was stirred for 30 min at room temperature. The solid product was collected by filtration, dried and recrystallised from methyl acetate to afford the title compound (2.12 g) as white needles, m.p. 196°–198°.

EXAMPLE 7

4β-Ethylamino-3,4,5,6-tetrahydro-2,6-methano-2-methyl-1-benzoxocin hydrochloride A solution of 4β-acetylamino-3,4,5,6-tetrahydro 2,6-methano-2-methyl-1-benzoxocin (4.41 g) is dry tetrahydrofuran (250 ml) was stirred, cooled in an ice-bath, and treated dropwise with a 1 M solution of borane-tetrahydrofuran complex (50 ml). The mixture was stirred and refluxed for 3 h, cooled in an ice-bath and treated with water (125 ml). The tetrahydrofuran was evaporated and the aqueous residue was treated with concentrated hydrochloric acid (40 ml) and heated 3 h on a steambath. The mixture was washed with ether, made basic by the addition of sodium hydroxide solution and extracted with ether. The extracts were dried (MgSO$_4$) and the solvent was evaporated to afford an oil which was further purified by column chromatography on silica gel using a chloroform: methanol mixture for elution.

The product, in dry ether, was treated with excess ethanolic hydrogen chloride and the white solid product was recrystallised from 2-propanol to afford the title compound (2.35 g) as colourless prisms m.p. 228°–230°. (Found: C, 67.0; H, 8.6; N, 5.0; Cl, 13.3. C$_{15}$H$_{22}$ClNO requires C, 67.3; H, 8.3; N, 5.2; Cl, 13.2%.)

EXAMPLE 8

3,4,5,6-Tetrahydro-2,6-methano-10-methoxy-2-methyl-4-oxo-1-benzoxocin

A stirred solution of 4-(2-hydroxy-3-methoxyphenyl)but-3-en-2-one (1 g) and ethyl acetoacetate (0.9 g) in ethanol (7 ml) was warmed to 40° and treated dropwise with sodium hydroxide solution (40%, 0.7 ml) over a period of 15 min. The mixture was heated under reflux for 9 h, then cooled and diluted with water. The solid (0.86 g) was collected by filtration. Crystallisation from ethyl acetate gave the title compound (0.46 g), m.p. 155°–156°.

EXAMPLE 9

3,4,5,6-Tetrahydro-2,6-methano-10-methoxy-2-methyl-4-oxo-1-benzoxocin oxime

A mixture of 3,4,5,6-tetrahydro-2,6-methano-10-methoxy-2-methyl-4-oxo-1-benzoxocin (1 g), hydroxylamine hydrochloride (0.33 g), pyridine (0.8 ml) and ethanol (10 ml) was heated under reflux for 1.5 h. The solvent was then evaporated under reduced pressure and water was added to the residue. The solid (0.66 g) was collected by filtration and crystallised from methanol to give the title compound (0.39 g), m.p. 181°–183°. (Found: C, 68.0; H, 7.15; N, 5.5. C$_{14}$H$_{17}$NO$_3$ requires C, 68.0; H, 6.9; N, 5.7%.)

EXAMPLE 10

4β-Amino-3,4,5,6-tetrahydro-2,6-methano-10-methoxy-2-methyl-1-benzoxocin hydrochloride A solution of 3,4,5,6-tetrahydro-2,6-methano-10-methoxy-2-methyl-4-oxo-1-benzoxocin oxime (2 g) and n-propanol (2.6 g) in dry tetrahydrofuran (80 ml) was added slowly with stirring to liquid ammonia (120 ml). Then sodium (0.77 g) in small portions was added, and after the addition was complete, the ammonia was evaporated and the residue was partitioned between ether and water. The ether layer was separated, washed with water, dried (MgSO$_4$), and evaporated. The residue (1.09 g) in anhydrous ether was treated with an ethanolic solution of hydrogen chloride (7 N., 1 ml). The solid was collected by filtration and washed with ether and then hot ethyl acetate. Crystallisation from a mixture of methanol and ethyl acetate gave the title compound (0.57 g), m.p. 279°–280°. (Found: C, 60.1; H, 7.9; Cl, 12.9; N, 5.1. C$_{14}$H$_{20}$ClNO$_2$.½H$_2$O requires C, 60.3; H, 7.6; Cl, 12.7; N, 5.0%.)

EXAMPLE 11

4β-Formylamino-3,4,5,6-tetrahydro-2,6-methano-10-methoxy-2-methyl-1-benzoxocin

Acetic anhydride (5 ml) was added to a stirred mixture of 4β-amino-3,4,5,6-tetrahydro-2,6-methano-10-methoxy-2-methyl-1-benzoxocin (1.3 g) and formic acid (15 ml) at 50°. After 4 h at this temperature the reaction was heated under reflux for 7 h. Acetic anhydride (2.5 ml) and formic acid (5 ml) were then added and heating under reflux was continued for a further 4 h. The solvent was removed under reduced pressure, acetic anhydride (5 ml) and formic acid (15 ml) were added to the residue and the mixture was heated under reflux for an additional 4 h. The solvent was again removed, water was added to the residue and the solid (0.96 g) was collected by filtration. Crystallisation from a mixture of methanol and ethyl acetate gave the title compound (0.74 g), m.p. 216°–218°.

EXAMPLE 12

3,4,5,6-Tetrahydro-2,6-methano-10-methoxy-2-methyl-4β-methylamino-1-benzoxocin hydrochloride.

4β-Formylamino-3,4,5,6-tetrahydro-2,6-methano-10-methoxy-2-methyl-1-benzoxocin (1.85 g) was reduced as in Example 4, except that the reaction was carried out in refluxing tetrahydrofuran for 3 h., to give the title compound (1.12 g), m.p. 284°–285° (decomp) (from methanol-ethyl acetate). (Found: C, 63.7; H, 7.5; Cl, 12.6; N, 4.9. C$_{15}$H$_{22}$ClNO$_2$ requires C, 63.5; H, 7.8; Cl, 12.5; N, 4.9%.)

EXAMPLE 13

3,4,5,6-Tetrahydro-2,6-methano-10-methoxy-2-methyl-4β-dimethylamino-1-benzoxocin hydrochloride Following the method of Example 2, but heating the reaction mixture on a steam bath for 2 h, 4β-amino-3,4,5,6-tetrahydro-2,6-methano-10-methoxy-2-methyl-1-benzoxocin (0.8 g) gave the title compound (0.68 g), m.p. 269°–271° (decomp) (from methanol-ethyl acetate). (Found: C, 64.2; H, 8.1; Cl, 11.8; N, 4.7. C$_{16}$H$_{24}$ClNO$_2$ requires C, 64.5; H, 8.1; Cl, 11.9; N, 4.7%.)

EXAMPLE 14

4β-Acetylamino-3,4,5,6-tetrahydro-2,6-methano-10-methoxy-2-methyl-1-benzoxocin

Acetyl chloride (2 ml) in anhydrous ether (20 ml) was added dropwise to an ice-cooled solution of 4β-amino-3,4,5,6-tetrahydro-2,6-methano-10-methoxy-2-methyl-1-benzoxocin (2 g) and triethylamine (2.5 ml) in ether (50 ml). After 1 h. the reaction mixture was filtered and the solid (1.76 g) was washed with 2 N-hydrochloric acid and then water. A portion (0.75 g) was crystallised from ethyl acetate to give the title compound (0.645 g), m.p. 206°–207.5°.

EXAMPLE 15

4β-Ethylamino-3,4,5,6-tetrahydro-2,6-methano-10-methoxy-2-methyl-1-benzoxocin hydrochloride 4β-Acetylamino-3,4,5,6-tetrahydro-2,6-methano-10-methoxy-2-methyl-1-benzoxocin (1 g) was reduced as in Example 4, except that the reaction was carried out in refluxing tetrahydrofuran for 3.5 h, to give, after treatment with ethanolic hydrogen chloride a solid (0.84 g) which was purified by preparative layer chromatography (using 10% solution of methanol in chloroform for development of the plates) to give the title compound (0.51 g), m.p. 194°–197° (decomp). (Found: C, 63.2; H, 8.2; Cl, 11.25; N, 4.7. $C_{16}H_{24}ClNO_2 \cdot \frac{1}{4}H_2O$ requires C, 63.6; H, 8.2; Cl, 11.7; N, 4.6%.)

EXAMPLE 16

4β-Bromoacetylamino-3,4,5,6-tetrahydro-2,6-methano-2-methyl-1-benzoxocin

Bromoacetyl bromide (2.52 g) in anhydrous ether (10 ml) was added to a stirred solution of 4β-amino-3,4,5,6-tetrahydro-2,6-methano-2-methyl-1-benzoxocin (2.03 g) and pyridine (1.1 ml) in anhydrous ether (20 ml) at −70°. The reaction mixture was then allowed to warm to room temperature and after 3 h ethyl acetate was added and the mixture was washed successively with water, 2 N-hydrochloric acid, water, sodium bicarbonate solution and water. The solution was then dried (MgSO$_4$) and evaporated. The residue was crystallised from ethyl acetate to give the title compound (1.65 g) m.p. 203°–204°.

EXAMPLE 17

4β-Aminoacetylamino-3,4,5,6-tetrahydro-2,6-methano-2-methyl-1-benzoxocin hydrochloride 4β-Bromoacetylamino-3,4,5,6-tetrahydro-2,6-methano-2-methyl-1benzoxocin (3.24 g) was added to a 30% solution of ammonia in methanol (30 ml) and after 18 h. the reaction mixture was evaporated to dryness and the residue was partitioned between ether and water. The ether layer was separated, dried and evaporated. The residue was purified by column chromatography and converted to the hydrochloride salt by treatment with ethanolic hydrogen chloride. Crystallisation from a mixture of isopropyl alcohol and ethyl acetate gave the title compound (0.7 g), m.p. 275°–277°. (Found: C, 60.3; H, 7.0; Cl, 11.7; N, 9.3. $C_{15}H_{21}ClN_2O_2$ requires C, 60.7; H, 7.1; Cl, 11.95; N, 9.4%.)

EXAMPLE 18

4β-(2-Bromopropionylamino)-3,4,5,6-tetrahydro-2,6-methano-2-methyl-1-benzoxocin

Prepared from 4β-amino-3,4,5,6-tetrahydro-2,6-methano-2-methyl-1-benzoxocin (3.05 g) as for the bromoacetylamino analogue of Example 16, but using 2-bromopropionyl bromide (4.3 g) to give the title compound (2.26 g) m.p. 173°–174° (isopropyl ether).

EXAMPLE 19

4β-(2-Aminopropionylamino)-3,4,5,6-tetrahydro-2,6-methano-2-methyl-1-benzoxocin hydrochloride Prepared from 4β-(2-bromopropionylamino)-3,4,5,6-tetrahydro-2,6-methano-2-methyl-1-benzoxocin (2.52 g) as for the aminoacethylamino analogue of Example 17 to give the title compound (0.63 g) m.p. 276°–278°. (Found: C, 61.8; H, 7.5; Cl, 11.2; N, 8.8. $C_{16}H_{23}ClN_2O_2$ required C, 61.8; H, 7.5; Cl, 11.4; N, 9.0%.)

EXAMPLE 20

(+)−4β-Amino-3,4,5,6-tetrahydro-2,6-methano-2-methyl-1-benzoxocin-(+)−hydrogen tartrate and (−)−4β-Amino-3,4,5,6-tetrahydro-2,6-methano-2-methyl-1-benzoxocin-(−)−hydrogen tartrate (+)−Tartaric acid (23.63 g) was dissolved in water (150 ml) with heating on a steam-bath. (±)−4β-amino-3,4,5,6-tetrahydro-2,6-methano-2-methyl-1-benzoxocin (30.49 g) was added to the hot solution. The mixture was shaken until it became homogeneous and then set aside at room temperature overnight. The crystalline solid which separated out was collected by filtration, washed with water (1×100 ml; 1×50 ml) at room temperature and dried, finally in vacuo, at 110° to afford (+)−4β-amino-3,4,5,6-tetrahydro-2,6-methano-2-methyl-1-benzoxocin-(+)−hydrogen tartrate (24.0 g) $[\alpha]_D^{22} +17.0°$ (c=1.0, H$_2$O). Recrystallisation from water (250 ml) afforded colourless needles (19.44 g), m.p. 218°–220° $[\alpha]_D^{22} +17.0°$ (c=1.0, H$_2$O).

The combined mother-liquors and washings were made alkaline (pH 11) by the addition of 40%-sodium hydroxide solution and the mixture was extracted (3×) with ether. The ethereal extracts were dried (anhyd. MgSO$_4$) and the solvent was evaporated under reduced pressure to afford a light-brown viscous oil (15.77 g). The product was treated with a hot solution of (−)tartaric acid (12.33 g), in water (100 ml). The mixture was shaken thoroughly and allowed to stand overnight at room temperature. The crystalline solid which separated out was collected by filtration, washed with water (50 ml) at room temperature and dried to constant weight in vacuo at 110° to afford (−)−4β-amino-3,4,5,6-tetrahydro-2,6-methano-2-methyl-1-benzoxocin-(−)−hydrogen tartrate (22.6 g), $[\alpha]_D^{22} -16.0°$ (c=1.0, H$_2$O). Recrystallisation from water (300 ml) afforded colourless plates (18.2 g), $[\alpha]_D^{22} -17.0°$ (c=1.0, H$_2$O) m.p. 218°–220°.

EXAMPLE 21

(−)−4β-Amino-3,4,5,6-tetrahydro-2,6-methano-2-methyl-1-benzoxocin (−)−4β-Amino-3,4,5,6-tetrahydro-2,6-methano-2-methyl-1-benzoxocin-(−)−hydrogen tartrate (17.10 g), was treated with water (300 ml) and the mixture was made alkaline (pH 11) by the addition of 40% sodium hydroxide solution. The oil which separated was extracted into ether and the extracts were combined and dried (anhyd. MgSO$_4$). The solvent was evaporated under reduced pressure to afford (−)−4β-amino-3,4,5,6-tetrahydro-2,6-methano-2-methyl-1-benzoxocin as a light-brown viscous oil (9.34 g), $[\alpha]_D^{22} -21.0°$ (c=1.0, EtOH).

EXAMPLE 22

(+)−4β-Amino-3,4,5,6-tetrahydro-2,6-methano-2-methyl-1-benzoxocin-(+)−hydrogen tartrate and (−)−4β-Amino-3,4,5,6-tetrahydro-2,6-methano-2-methyl-1-benzoxocin-(+)−hydrogen tartrate (+)−Tartaric acid (22.80 g), was dissolved in water (145 ml) with heating on a steam-bath. (±)−4β-Amino-3,4,5,6-tetrahydro-2,6-methano-2-methyl-1-benzoxocin (29.44 g), was added to the hot solution. The mixture was shaken until it became homogeneous and was set aside at room temperature overnight. The crystalline solid which separated out was collected by filtration, washed with water (1×100 ml; 1×50 ml) at room temperature and dried. Recrystallisation from water afforded (+)−4β-amino-3,4,5,6-tetrahydro-2,6-methano-2-methyl-1-benzoxocin-(+)-hydrogen tartrate as colourless columns (20.84 g), $[\alpha]_D^{22} +16.5°$ (c=1.0, H$_2$O).

The mother-liquors and washings were combined and evaporated to dryness under reduced pressure. The white solid residue was recrystallised from methanol to afford (−)−4β-amino-3,4,5,6-tetrahydro-2,6-methano- 2-methyl-1-benzoxocin-(+)-hydrogen tartrate as colourless prisms (17.23 g) $[\alpha]_D^{22}+8.0°$ (c=1.0, H$_2$O).

EXAMPLE 23

(−)−4β-Aminoacetylamino-3,4,5,6-tetrahydro-2,6-methano-2-methyl-1-benzoxocin hydrochloride (a)

(−)−4β-Bromoacetylamino-3,4,5,6-tetrahydro-2,6-methano-2-methyl-1-benzoxocin (−)−4β-Amino-3,4,5,6-tetrahydro-2,6-methano-2-methyl-1-benzoxocin (4.065 g), was dissolved in dry ether (125 ml) containing pyridine (3.16 g). The solution was stirred and cooled to −78° in an acetone/CO$_2$ bath. A solution of bromoacetyl bromide (4.85 g), in dry ether (30 ml) was added dropwise with stirring to the cold solution over a period of 1h. When the addition was complete, the cooling bath was removed and the mixture was allowed to attain room temperature. The reaction mixture was stirred at room temperature for 2h and was then shaken with water (100 ml). The white solid precipitate was collected by filtration, washed with water and ether and dried, finally in vacuo, to constant weight. Recrystallisation from methanol afforded the title compound (5.72 g), as colourless columns m.p. 238°–240°. $[\alpha]_D^{22}-19.5°$ (c=1.0, DMSO).

(b)

(−)−4β-Aminoacetylamino-3,4,5,6-tetrahydro-2,6-methano-2-methyl-1-benzoxocin hydrochloride (−)−4β-Bromoacetylamino-3,4,5,6-tetrahydro-2,6-methano-2-methyl-1-benzoxocin (4.70 g), was added at room temperature to a stirred solution of distilled anhydrous ammonia (80 ml) in methanol (400 ml). The mixture was stoppered and stirred for 3h at room temperature. The mixture was evaporated to dryness under reduced pressure and the residual oil was taken up in chloroform (200 ml). The solution was filtered and the filtrate was shaken with water (30 ml). The mixture was treated with 2 N-sodium hydroxide solution until the aqueous layer was strongly alkaline (pH 11). The mixture was again shaken and the chloroform layer was separated. The aqueous phase was extracted with fresh chloroform. The organic solutions were combined, washed (2×) with brine and dried (anhyd. MgSO$_4$). The solvent was evaporated under reduced pressure to afford a white foam.

The foam was dissolved in absolute ethanol (70 ml). The solution was cooled in an ice-bath and treated with a small excess of hydrogen chloride from a standard ethanolic solution. The mixture was stirred for 30 min in an ice-bath and subsequently for 1h at room temperature. The solvent was removed by evaporation under reduced pressure to afford a white foam. Crystallisation from methanol/ether afforded the title compound (3.34 g), as colourless needles $[\alpha]_D^{22}-17.0°$ (c=2.0, H$_2$O), m.p. 230°.

EXAMPLE 24

(a) 4-(2-Chloro-6-hydroxyphenyl)but-3-en-2-one

2-Chloro-6-hydroxybenzaldehyde (20.57 g) was treated with 10% sodium hydroxide solution (52.5 ml) and the mixture was shaken. Acetone (44.6 ml) and a further portion of 10% sodium hydroxide (71 ml) were added. After shaking again, the mixture was diluted with water (500 ml) and stirred overnight at room temperature.

The mixture was acidified to pH 1 by the addition of 2 N hydrochloric acid and the solid product was collected by filtration, washed with water and dried (24.68 g).

A small sample was purified by preparative-layer chromatography on silica gel using a chloroform methanol mixture for elution, and recrystallisation from methylene chloride, to give the title compound as pale yellow needles m.p. 153°–155°.

(b)

7-Chloro-3,4,5,6-tetrahydro-2,6-methano-2-methyl-4-oxo-1-benzoxocin 4-(2-Chloro-6-hydroxyphenyl)but-3-en-2-one (2.0 g) was treated with ethanol (10 ml), 40% sodium hydroxide solution (2.2 ml) and acetylacetone (1.8 g). The mixture was stirred and heated under reflux for 30 min. A further addition of acetylacetone (1.8 g) was made and the mixture was stirred and refluxed for a further period of 4h. The mixture was diluted with water (200 ml) and extracted with ether. The extracts were dried and the solvent was removed under reduced pressure. The residue was purified by preparative-layer chromatography on silica gel using a chloroform-methanol mixture for elution and subsequent recrystallisation from petroleum ether (b.p. 60°–80°) to afford the title compound (0.95 g) m.p. 98°–100°.

EXAMPLE 25

(a)

7-Chloro-3,4,5,6-tetrahydro-2,6-methano-2-methyl-4-oxo-1-benzoxocin O-Methyloxime 7-Chloro-3,4,5,6-tetrahydro-2,6-methano-2-methyl-4-oxo-1-benzoxocin (13.76 g), methoxyamine hydrochloride (5.35 g) and pyridine (4.5 ml) were dissolved in ethanol (250 ml) and the mixture was heated 1h on a steam-bath. The hot solution was filtered and allowed to stand overnight at 5°. The crystalline solid which separated out was collected by filtration and dried. The mother-liquors were concentrated under reduced pressure and diluted with water. The mixture was extracted with ether, dried and the solvent was removed under reduced pressure. The residue was purified by preparative-layer chromatography on silica gel using chloroform for elution to afford a further sample of crystalline solid. The two samples were combined and recrystallised from ethanol to afford the title compound (13.32 g) m.p. 151°–4°.

(b)

4β-Amino-7-chloro-3,4,5,6-tetrahydro-2,6-methano-2-methyl-1-benzoxocin Hydrochloride A 1 M solution of borane-tetrahydrofuran complex in tetrahydrofuran (95 ml) was added dropwise with stirring to an ice-cooled solution of 7-chloro-3,4,5,6-tetrahydro-2,6-methano-2-methyl-4-oxo-1-benzoxocin O-methyloxime (13.0 g) in tetrahydrofuran (240 ml). When the addition was complete, the mixture was heated under reflux with stirring for 4.5h and then allowed to stand overnight at room temperature. The mixture was cooled in an ice-bath with stirring, water (150 ml) was added and the mixture was stirred at room temperature for 30 min. The tetrahydrofuran was removed by evaporation under reduced pressure and the residue was treated with a solution of concentrated hydrochloric acid (27 ml) in water (80 ml). The acidic mixture was heated 2h on a steam-bath, cooled to room temperature, washed with ether and made alkaline (pH 11) by the addition of 40% sodium hydroxide solution. The mixture was extracted with ether, the extracts were dried and the solvent was evaporated under reduced pressure to afford a colourless oil (11.15 g) which consisted of a mixture of the 4α and 4β amines. The required isomer was separated by preparative-layer chromatography using a mixture of chloroform and methanol for elution. Treatment of the free base with hydrogen chloride as described in Example 1 (Method A) and recrystallisation of the product from a mixture of ethanol and ether afforded the title compound (1.22 g) as colourless prisms m.p. 331°. (Found: C, 56.7; H, 6.3; N, 4.8; Cl, 25.3. $C_{13}H_{17}Cl_2NO$ requires C, 56.9; H, 6.25; N, 5.1; Cl, 25.9%.)

EXAMPLE 26

(a) 5-(2-Hydroxyphenyl)-1,3-cyclohexanedione 5-(2-Methoxyphenyl)-1,3-cyclohexanedione (15.0 g) was suspended in methylene chloride (150 ml). The mixture was cooled to −78° with stirring and a solution of boron tribromide (39.3 g) in methylene chloride (75 ml) was added dropwise over 1h. The mixture was stirred at −78° for 45 min after the addition was complete and at room temperature for a further 18h. Excess water was added and the mixture was stirred vigorously at room temperature for 4h. The solid which separated out was collected by filtration, washed with water and dried to afford the title dione (12.0 g). Recrystallisation from aqueous ethanol afforded white prisms m.p. 190°–192°.

(b) 3-Ethoxy-5-(2-hydroxyphenyl)-2-cyclohexenone 5-(2-Hydroxyphenyl)-1,3-cyclohexanedione (5.0 g) was dissolved in ethanol (225 ml). The solution was heated under reflux for 3h and diluted to 2 l. by the addition of water. The solid which separated out was collected by filtration, washed with water and dried. Recrystallisation from ethanol afforded the title compound (1.5 g) as pale yellow prisms m.p. 194°–197°.

EXAMPLE 27

(a) 3-Ethoxy-5-(2-methoxyethoxymethoxyphenyl)-2-cyclohexenone

A suspension of 3-ethoxy-5-(2-hydroxyphenyl)-2-cyclohexenone (32.4 g) in tetrahydrofuran (400 ml) was added slowly to an ice-cooled suspension of sodium hydride (3.34 g) in tetrahydrofuran (75 ml). The mixture was stirred at room temperature for 30 min, cooled in an ice-bath and a solution of methoxyethoxymethyl chloride (20.8 g) in tetrahydrofuran (50 ml) was added dropwise with stirring. The mixture was stirred overnight at room temperature and then was concentrated by the removal of most of the tetrahydrofuran under reduced pressure. The concentrate was diluted with water and extracted with ether. The ethereal extracts were dried and the solvent removed under reduced pressure. The residual oil was purified by column chromatography on silica gel using chloroform for elution to afford the title compound (36.23 g) as a pale yellow oil.

(b) 3-Ethyl-5-(2-methoxyethoxymethoxyphenyl)-2-cyclohexenone

A solution of 3-ethoxy-5-(2-methoxyethoxymethoxyphenyl)-2-cyclohexenone (2.0 g) in benzene (60 ml) was added dropwise with stirring in an atmosphere of dry nitrogen to an ice-cooled 1.5 M solution of ethyllithium in benzene (20.8 ml). When the addition was complete, water was added and the mixture was allowed to stand overnight at room temperature. The benzene layer was separated and the aqueous layer was extracted with ether. The organic solutions were combined, dried and the solvents were evaporated under reduced pressure. The residue was purified by preparative-layer chromatography on silica gel using a mixture of ethyl acetate and petroleum ether (b.p. 60°–80°) for elution to afford the title compound (0.65 g) as a pale yellow oil. (Found: C, 70.9; H, 7.7. $C_{18}H_{24}O_4$ requires C, 71.0; H, 7.9%.)

EXAMPLE 28

2-Ethyl-3,4,5,6-tetrahydro-2,6-methano-4-oxo-1-benzoxocin

A solution of titanium tetrachloride (3.7 ml) in methylene chloride (9 ml) was added dropwise with stirring to an ice-cooled solution of 3-ethyl-5-(2-methoxyethoxymethoxyphenyl)-2-cyclohexenone (9.23 g) in tetrahydrofuran (180 ml). The mixture was stirred at 0° for 30 min and subsequently for 24h at room temperature. Water was added and the mixture was stirred for 2h and extracted with ether. The extracts were dried and the solvent was removed under reduced pressure. The residue was purified by preparative-layer chromatography on silica gel using a mixture of chloroform and methanol for elution to afford the title compound (3.64 g). Recrystallisation from methanol afforded white columns m.p. 116°–118°.

EXAMPLE 29

(a) 2-Ethyl-3,4,5,6-tetrahydro-2,6-methano-4-oxo-1-benzoxocin Oxime

Prepared from 2-ethyl-3,4,5,6-tetrahydro-2,6-methano-4-oxo-1-benzoxocin (3.80 g) following the procedure described in Example 9. The product was purified by preparative-layer chromatography on silica gel using a mixture of chloroform and methanol for elution to afford the title compound (2.62 g). Recrystallisation from petroleum ether (b.p. 80°–100°) gave white needles m.p. 145°–148°.

(b) 4β-Amino-2-ethyl-3,4,5,6-tetrahydro-2,6-methano-1-benzoxocin Hydrochloride

Prepared from 2-ethyl-3,4,5,6-tetrahydro-2,6-methano-4-oxo-1-benzoxocin oxime (2.30 g) using the procedure described in Example 10 to give the title compound (0.89 g) as white plates m.p. 256°–259°. (Found: C, 66.2; H, 8.1; N, 5.4; Cl, 13.9. $C_{14}H_{20}ClNO$ requires C, 66.3; H, 7.9; N, 5.5; Cl, 14.0%.)

EXAMPLE 30

(a) 4β-Benzyloxycarbonylglycylglyclamino)-3,4,5,6-tetrahydro-2,6-methano-2-methyl-1-benzoxocin A mixture of 4β-amino-3,4,5,6-tetrahydro-2,6-methano-2-methyl-1-benzoxocin (3.3 g), N-benzyloxycarbonylglycylglycine (4.3 g), N,N¹-dicyclohexylcarbodiimide (3.5 g), and methylene chloride (54 ml) was stirred for 22h. Acetic acid (¾ drops) was then added and after ½h the mixture was filtered. The solid was washed with hot chloroform and then hot ethyl acetate. Crystallisation from ethanol gave the title compound (2.96 g) m.p. 197°–198°, (Found: C, 66.4; H, 6.5; N, 9.2. $C_{25}H_{29}N_3O_5$ requires C, 66.5; H, 6.5; N, 9.3%.)

(b)

4β-Glycylglycylamino-3,4,5,6-tetrahydro-2,6-methano-2-methyl-1-benzoxocin hydrochloride A stream of hydrogen was passed over a stirred mixture of 4β-(benzyloxycarbonylglycylglycylamino)-3,4,5,6-tetrahydro-2,6-methano-2-methyl-1-benzoxocin (2.93 g), 5% palladium on charcoal (2 g), acetic acid (5 drops) and ethanol (280 ml) for 5h. The reaction mixture was then filtered and the filtrate evaporated. The residue (1.99 g) was converted to the hydrochloride salt and crystallised from a mixture of methanol and ethyl acetate to give the title compound (1.56 g), m.p. 243°–244°. (Found: C, 56.3; H, 6.8; Cl, 10.3; N, 11.7. $C_{17}H_{24}ClN_3O_3 \cdot \frac{1}{2} H_2O$ requires C, 56.3; H, 6.9; Cl, 9.8; N, 11.6%.)

EXAMPLE 31

10-Ethoxy-3,4,5,6-tetrahydro-2,6-methano-2-methyl-4-oxo-1-benzoxocin

A mixture of 4-(3-ethoxy-2-hydroxyphenyl)-but-3-ene-2-one (5 g), ethanol (25 ml), 40% sodium hydroxide solution (5.5 ml) and acetyl acetone (4.5 ml) was heated under reflux for 30 min. Acetyl acetone (4.5 ml) was added and the mixture was heated for a further 2h. The reaction mixture was then partitioned between ethyl acetate and water. The organic phase was separated, dried and evaporated. The residue (5.38 g) was purified by column chromatography using 2% methanol in chloroform as eluent. A portion (1.42 g) of this product (3.28 g) was crystallised from ethyl acetate to give the title compound (0.6 g) m.p. 136°.

EXAMPLE 32

10-Ethoxy-3,4,5,6-tetrahydro-2,6-methano-2-methyl-4-oxo-1-benzoxocin oxime

A mixture of 10-ethoxy-3,4,5,6-tetrahydro-2,6-methano-2-methyl-4-oxo-1-benzoxocin (2.56 g), hydroxylamine hydrochloride (2.17 g), pyridine (2.52 ml) and ethanol (20 ml) was heated under reflux for 3h. The reaction mixture was then evaporated and the residue partitioned between ethyl acetate and water. The organic phase was separated, dried and evaporated. The residue (2.8 g) was crystallised from methanol to give the title compound (1.05 g) m.p. 131°.

EXAMPLE 33

4β-Amino-10-ethoxy-3,4,5,6-tetrahydro-2,6-methano-2-methyl-1-benzoxocin hydrochloride Prepared from 10-ethoxy-3,4,5,6-tetrahydro-2,6-methano-2-methyl-4-oxo-1-benzoxocin oxime (2.59 g) as for Example 10 to give the title compound (1.2 g), m.p. 284°–286° (isopropanol/ethyl acetate). (Found: C, 63.7; H, 8.0; Cl, 12.5; N, 5.0. $C_{15}H_{22}ClNO_2$ requires C, 63.5; H, 7.8; Cl, 12.5; N, 4.9%.)

EXAMPLES OF PHARMACEUTICAL COMPOSITIONS

| Tablets | |
|---|---|
| Active ingredient | 200 mg |
| Microcrystalline Cellulose (Avicel) | 80 mg |
| Maize starch or Explotab* | 24 mg |
| Magnesium stearate | 5 mg |

| -continued | |
|---|---|
| Tablets | |
| Tablet weight | 309 mg |

*Explotab is a Trade Mark for sodium starch glycollate

The active ingredient is mixed with part of the magnesium stearate, and densified using either a roller compactor (Hutt) or a heavy duty tablet press. The compacts are 'broken' by passing through a set of sieves. The remaining ingredients are blended and tablets of appropriate size compressed on rotary machines.

The tablets may be coated with a thin cellulose film and a pigment may be included in the film.

| Capsules | |
|---|---|
| Active ingredient | 200 mg |
| Lactose | 80 mg |
| Maize starch or Explotab (Trade Mark) | 15 mg |
| Magnesium stearate | 5 mg |

The active ingredient is blended with the excipients in a suitable blender, using a gradual dilution technique. The blend is filled in suitable (preferably size 1 or 2) capsules using an automatic machine (eg Zanasi).

The drug may be milled prior to incorporation in tablet or capsule formulation.

I claim:

1. A compound of general formula (I):

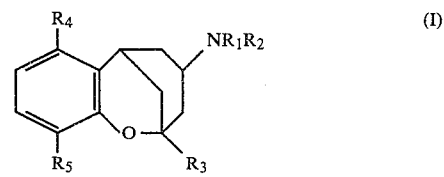

wherein
   $R_1$ represents a hydrogen atom or $C_{1-4}$ alkyl or $C_{2-4}$ alkenyl group, or the group $COANH_2$, $CSANH_2$, or $COANHCOCH_2NH_2$ in which A is methylene optionally substituted by a $C_{1-3}$ alkyl group; and
   $R_2$ represents a hydrogen atom or a $C_{1-4}$ alkyl group; or $NR_1R_2$ forms a piperidino, piperazino or N-methylpiperazino group;
   $R_3$ represents a $C_{1-4}$ alkyl group or a benzyl group;
   $R_4$ represents a hydrogen or halogen atom; and
   $R_5$ represents a hydrogen atom or a $C_{1-4}$ alkyl or $C_{1-4}$ alkoxy group, with the proviso that one of $R_4$ and $R_5$ is a hydrogen atom
and physiologically acceptable salts thereof.

2. A compound according to claim 1 wherein $R_1$ is a hydrogen atom or an alkyl group, aminoacetyl, 2-aminopropionyl or glycylglycyl; and
   $R_2$ is a hydrogen atom or an alkyl group; or
   $NR_1R_2$ is piperidino;
   $R_3$ is an alkyl group;
   $R_4$ is a hydrogen or chlorine atom;
   $R_5$ is a hydrogen atom or an alkoxy group.

3. A compound according to claim 1 wherein
   $R_1$ is a hydrogen atom or an aminoacetyl group;
   $R_2$, $R_4$ and $R_5$ are hydrogen atoms; and
   $R_3$ is a methyl group.

4. 4β-Amino-3,4,5,6-tetrahydro-2,6-methano-2-methyl-1-benzoxocin and its physiologically acceptable salts.

5. 4β-Aminoacetylamino-3,4,5,6-tetrahydro-2,6-methano-2-methyl-1-benzoxocin and its physiologically acceptable salts.

6. A compound according to claim 5 which is the levorotatory(−)enantiomer.

7. An anxiolytic and anti-convulsant pharmaceutical composition which comprises an anxiolytic and anti-convulsant effective amount of at least one compound according to claim 1 together with a pharmaceutically acceptable carrier or diluent therefor.

8. A pharmaceutical composition according to claim 7 which is formulated in unit dosage form containing from 10 to 200 mg of active ingredient per dosage unit.

9. A method for the treatment of a patient suffering from anxiety and/or convulsions which comprises administering to the patient an anxiolytic or anti-convulsant effective amount of a compound according to claim 1.